US007153841B2

(12) United States Patent
Roncucci et al.

(10) Patent No.: US 7,153,841 B2
(45) Date of Patent: Dec. 26, 2006

(54) METAL SUBSTITUTED NON-CENTROSIMMETRICAL PHTHALOCYANINE ANALOGUES, THEIR PREPARATION AND USE IN PHOTODYNAMIC THERAPY AND IN VIVO DIAGNOSTIC

(75) Inventors: Gabrio Roncucci, Colle Val D'Elsa (IT); Donata Dei, San Gimignano (IT); Maria Paola De Filippis, Florence (IT); Lia Fantetti, Florence (IT); Daniele Nistri, Prato (IT)

(73) Assignee: L. Molteni & C. Dei Fratelli Alitti Societa Di Esercizio S.p.A., Scandicci (IT)

( * ) Notice: Subject to any disclaimer, the term of this patent is extended or adjusted under 35 U.S.C. 154(b) by 40 days.

(21) Appl. No.: 10/472,882

(22) PCT Filed: Mar. 20, 2002

(86) PCT No.: PCT/EP02/03108

§ 371 (c)(1),
(2), (4) Date: Apr. 1, 2004

(87) PCT Pub. No.: WO02/090361

PCT Pub. Date: Nov. 14, 2002

(65) Prior Publication Data

US 2004/0156787 A1    Aug. 12, 2004

(30) Foreign Application Priority Data

Mar. 21, 2001   (EP)   ................................. 01106411

(51) Int. Cl.
*A61K 31/695*   (2006.01)
*A61K 31/555*   (2006.01)
*A61K 49/10*    (2006.01)

(52) U.S. Cl. ........................ 514/63; 514/185; 540/124; 540/125

(58) Field of Classification Search .................. 514/63, 514/185; 540/124, 125
See application file for complete search history.

(56) References Cited

FOREIGN PATENT DOCUMENTS

| EP | 0906758 A | 4/1999 |
|---|---|---|
| EP | 0906758 | * 7/1999 |
| EP | 1164135 A | 12/2001 |

OTHER PUBLICATIONS

Sastre, A. et al., "Synthesis of Novel Unsymmetrical Monoaminated Phthalocyanines," Tetrahedron Letters, vol. 36 (No. 46), p. 8501-8504, (Nov. 13, 1995).
Hu, M. et al., "Hydroxyphtalocyanines as Potential Agents for Cancer Therapy," J. Med. Chem, p. 1789-1802, (1998).
Herter, R. et al., "Synthesis of NIR-Absorbing Monofunctionalized Phtalocyanines via Copolymer Coupling," Proc. Spie-Int. Soc. Opt. Eng., vol. 2625, p. 384-385, (1996).
Savitskii, A. P. et al., "Avidin-Biotin System as an Agent for Targeted Delivery of Antitumor Agents," Ross. Khim. Zh., vol. 42 ( No. 5), p. 77-83, (1998).
Leznoff, C. C. et al., "The Synthesis of a Soluble, Unsymmetrical Phthalocyanine of a Polymer Support," Tetrahedron Letters, vol. 23 ( No. 30), p. 3023-3026, (1982).
Reimlinger, H., "Nomeklatur Organisch-Chemischer Verbindungen," Walter de Gruyter, p. 80-82, (Sep. 19, 1998).

* cited by examiner

*Primary Examiner*—Shaojia Jiang
*Assistant Examiner*—Ganapathy Krishnan
(74) *Attorney, Agent, or Firm*—Wolf, Greenfield & Sacks, P.C.

(57) ABSTRACT

Phthalocyanine analogues having an active group able to link the phthalocyanine t carriers molecules and phthalocyanine to carriers molecules and phthalocyanine analogues as phthalocyanine-carrier conjugates showing enhanced photodynamic properties, red shifted absorption characteristic, all useful for photodynamic therapy, are described.

Photosensitizers themselves or the photosensitizers-carriers conjugates are useful compounds either for treatment of various infectious diseases, the in vivo eradication of microorganisms as well as diseases characterized by cellular hyperproliferation, in particular tumours psoriasis, actinic keratosis, atheromas, endoarterial hyperplasia and prostate hyperplasia.

The above compounds can be also useful for blood and blood derivatives sterilization and in vivo/vitro diagnostics.

11 Claims, 1 Drawing Sheet

METAL SUBSTITUTED NON-CENTROSIMMETRICAL PHTHALOCYANINE ANALOGUES, THEIR PREPARATION AND USE IN PHOTODYNAMIC THERAPY AND IN VIVO DIAGNOSTIC

CROSS-REFERENCES TO RELATED APPLICATIONS

This application is a national phase filing of international application no. PCT/EP02/03108, filed Mar. 20, 2002, which claims priority to European Application No. 01106411.0, filed Mar. 21, 2001. All of the foregoing applications are hereby incorporated by reference to the extent permitted by law.

FIELD OF THE INVENTION

The invention relates to non-centrosymmetrical Me-phthalocyanine analogues having a site specific reactive group able to link them to biological carriers through covalent bonds, good solubility and enhanced photodynamic properties.

The invention refers also to conjugates consisting of metal-phthalocyanine analogues as above defined and amino acids, polypeptides, proteins, antibodies, polysaccharides and aptamers.

Moreover the invention refers to processes for preparing the above said products and to pharmaceutical compositions containing them, useful for in vivo/ex vivo therapeutic treatment and in vitro/in vivo diagnostic purposes.

STATE OF THE ART

It is known that organic molecules able to produce singlet oxygen, as a result of light irradiation, may have photoenhanced biocidal activity. The biocidal properties of such molecules, occurring with essentially every living form, make these molecules extremely interesting for therapeutic applications.

The practical application of photosensitizers is generally limited due to the fact that those products are either allergens, in some cases are retained in human skin or non specifically localized in ill tissues, thus leading to phototoxicity after light exposition.

Early work in the 1970's, followed from studies in the 1980's, have shown that photosensitizers can be used against viruses, fungi, bacteria and eukaryote cells. Dougherty et al. (Cancer Res., 1978, 38, 262) has pioneered the field of PDT for tumour treatment with photoactivatable dyes in association with long wavelength radiation.

Even if a great deal of advancements in this field have been performed, there is still a need for new compounds to be used both in PDT therapy of infectious diseases and tumour conditions.

Deficiencies of earlier agents, based on naturally-occurring starting materials, can be overcome by using synthetic chemically pure photoactivatable products, more readily prone to further chemical structural modifications.

Among the new various photosensitizers, so called "second generation photosensitizers", worth of further development, phthalocyanines, short name of tetrabenzotetraaza porphyrins, appear ones of the most important photosensitizers for therapeutic applications.

Zn(II)-phthalocyanines having applications in photodynamic therapy (PDT) and diagnosis are described in EP 906 758, in the name of the same Applicant.

The therein described products show very interesting properties, in fact can be easily prepared, have a low intrinsic toxicity (dark toxicity), while they are active as photosensitizers for singlet oxygen production or radicals, are selectively up-taken in proliferating cells, rapidly degraded and eliminated from non target tissues after administration and finally, are available as chemically pure and stable compounds, eventually prone to further synthetic modification in order to be more selective.

In order to further improve the therapeutic potential of these photosensitizers, they are specifically designed in order to be easily linked to carriers able by themselves to specifically recognize biological targets, thus providing the way to reach the living form to be eradicated, while not affecting the surrounding healthy cells.

In particular, in order to allow chemical conjugation to biological relevant macromolecular carriers, the phthalocyanines should bear reactive functions, specific for only one functional group of the macromolecule and hydrophilic groups, with the aim of not introducing variation in the overall hydrophilic nature of the conjugate. Moreover the presence of suitable substituents should not interfere with the photodynamic properties of phthalocyanine.

It must be noted that previously described phthalocyanines are not suitable for linking to biologically relevant carriers because they lack specific reactive groups, therefore no reaction can occur unless cross linking reagents especially devised are used, or they have more than one reactive groups and therefore their use in the conjugation procedures results in an uncontrolled proteins polymerization and crosslinking which in turn, leads to difficulty to purify and analyse conjugates preparation.

Organic solvents soluble, hydrophobic phthalocyanines bearing one reactive group have been previously described (H. Kliesh et al. Liebigs Ann. 1995,1269–1273), however the overall hydrophobic properties of these phthalocyanines cause a modification of the macromolecular hydrophilic balance, have a negative effect on the conjugate stability, may cause irreversible aggregation problems and lead to carriers denaturation.

In view of the above said, it is essential to provide new products having both physical-chemical and photodynamic enhanced properties, thus allowing their use against a wider spectrum of pathologies, while lowering the undesired side effects that were both accomplished with the products described in this invention.

SUMMARY OF THE INVENTION

The present invention refers to Me-phthalocyanines analogues of formula (I)

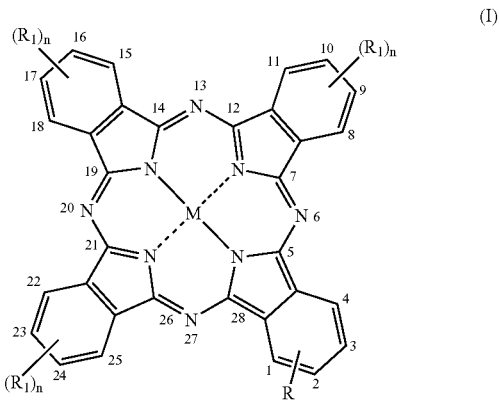

wherein:

n is 1, 2 or 4;

M is chosen in the group consisting of Zn, $Si(OR_7)_2$ and $AlOR_7$ wherein $R_7$ is chosen in the group consisting of H, $C_{1-15}$ alkyl and pharmaceutically acceptable salts thereof;

R is chosen in the groups consisting of: —COOH, —SH, —OH, —$NH_2$, —CO—CH2—Br, —$SO_2Cl$, maleimide, hydrazide, phenol, imidate, biotine, possibly bound to the phthalocyanine nucleus through a suitable linker and $R_1$ is H or, when n=2 and the two groups $R_1$ are in the positions 9,10,16,17,23,24, said two groups $R_1$ can form a saturated or unsaturated heterocycle, possibly substituted, which may contain up to two heteroatoms chosen from N,O, S; or $R_1$ is represented by the group $(X)_pR_2$, wherein:

X is chosen in the group consisting of O, S, —$NR_5$ and —$CH_2$— and $R_2$ is

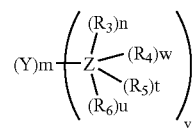

where:

Y is chosen in the group consisting of $C_{1-10}$ alkyl and phenyl, possibly substituted, or it forms with the Z group, to which it is bound, a saturated or unsaturated heterocycle, possibly substituted, which may contain up to two heteroatoms chosen in the group consisting of N, O and S;

Z is chosen in the group consisting of —N, —$CH_2N$ and —$CONHCH_2CH_2N$;

$R_3$ and $R_4$, equal or different from one another, are chosen in the group consisting of $C_{1-15}$ alkyl and phenyl, or form with the Z group, to which they are bound, a saturated or unsaturated heterocycle, possibly substituted, which may contain up to two heteroatoms chosen in the group consisting of N, O and S;

$R_5$ and $R_6$, equal or different from one another, are chosen in the group consisting of H and $C_{1-15}$ alkyl;

m, n, p, w, t and u, independently from one another, are 0 or 1; and v is an integer comprised between 1 and 3;

with the proviso that:

R is in the position 1 or 2.

$R_1$ is in the positions: 8(11), 15(18), 22(25), or 9(10), 16(17), 23(24) when n=1.

$R_1$ is in the positions: 8,11,15,18,22,25 or 9,10,16,17,23,24 when n=2.

The invention refers also to the compounds of formula (I) as above defined conjugated with bio-organic carriers such as amino acids, polypeptides, proteins polysaccharides and aptamers.

DETAILED DESCRIPTION OF THE INVENTION

Figure 1:
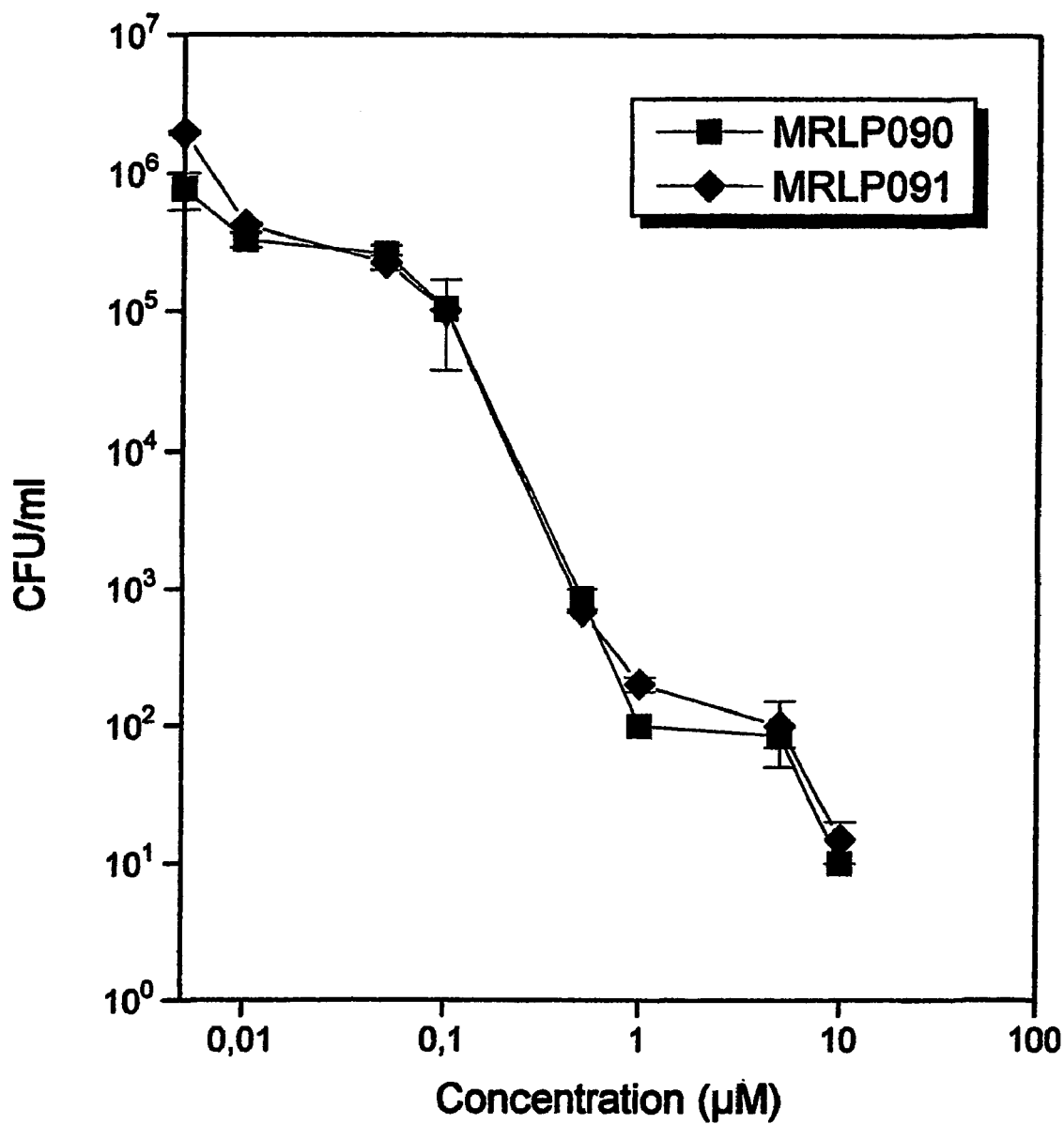
FIG. 1 represents the variation of the colony forming units (CFU) of *C. albicans* vs. the concentration (μM) of the compounds according to Examples 7 and 8, indicated in the FIGURE as MRLP 090 and MRLP 091 respectively.

The present invention allows to overcome the above said problem thanks to the compounds of formula (I) as above defined.

According to the present invention Zn(II)-phthalocyanines are preferred wherein R is as previously defined, and $R_1$ is represented by the group $(X)_pR_2$, previously defined.

According to the invention, the definition "suitable linker" it is intended in the sense commonly given to this definition in the field of protein and nucleic acid modification (S. S. Wang, Chemistry of Protein Conjugation and Cross-Linking CRC Press, Inc. 1993, G. T. Hermanson Bioconjugate Techniques Academic Press, 1996) i.e. an aliphatic or aromatic moiety which act as a spacer between the phthalocyanine nucleus and the biological macromolecules, in order to satisfy wanted sterical and/or structural requirements.

By saturated or unsaturated heterocycle possibly substituted, as defined in the above general formula, the following are preferably meant: morpholine, piperidine, pyridine, pyrimidine, piperazine, pyrrolidine, pyrroline, imidazole, aniline, and julolidine (2,3,6,7-tetrahydro-1H,5H-pyrido[3,2,1-ij]quinoline).

According to the invention, the preferred products are those in which the group $(X)_pR_2$ contains substituents bearing tertiary or quaternary nitrogen. In particular, the said group $(X)_pR_2$ is preferably represented by:

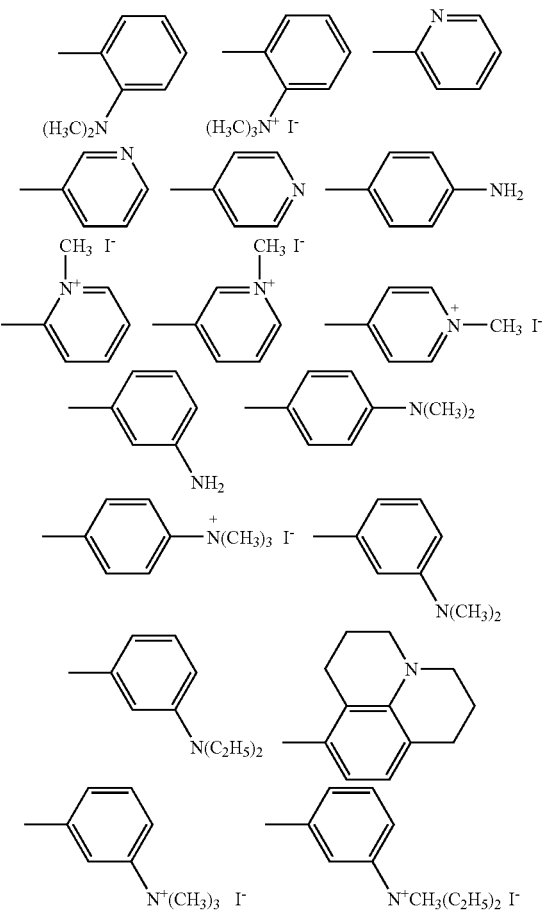

-continued

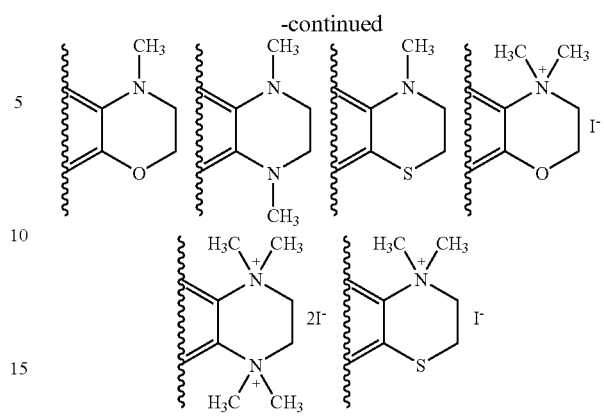
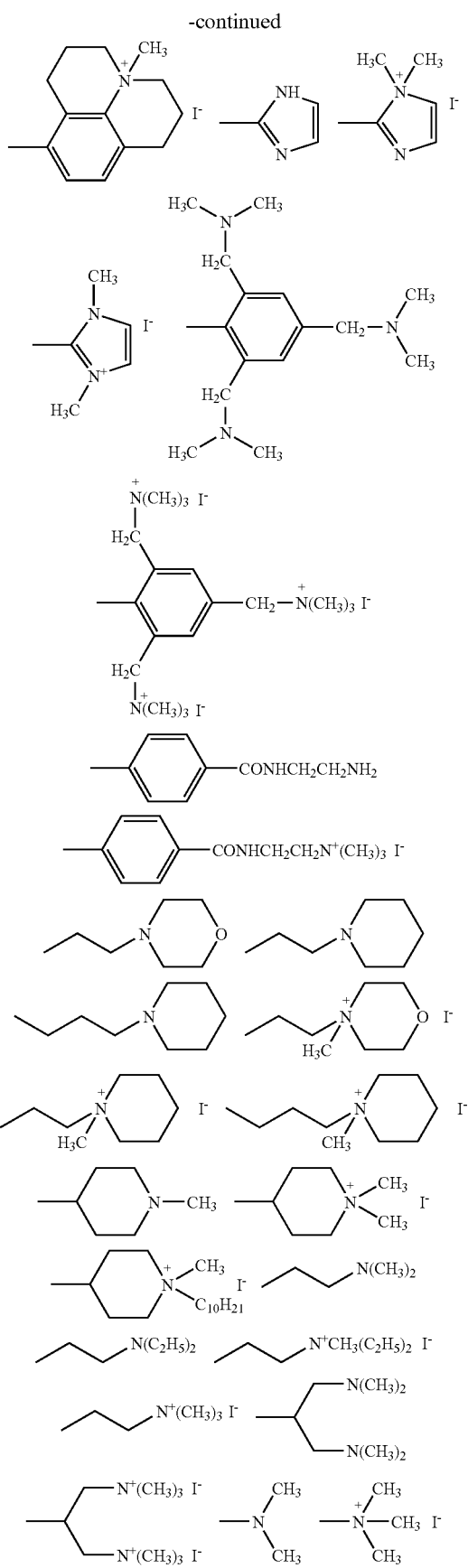

The compound in the present invention can be prepared in homogeneous as well heterogeneous phase, according to synthesis known in organic chemistry (and also described in the above cited patent) as well as by using the sub-phthalocyanine route.

Cationic phthalocyanines of formula (I) can be prepared by reacting the corresponding neutral compounds previously described, with an excess of alkyl iodide, with or without organic solvents, at temperature comprised between room temperature and reflux, for a time comprised between 1 h and 200 h. Pharmaceutically acceptable salts of the phthalocyanine compounds of the present invention, bearing basic substituents, include conventional acid addition salts, obtained by the addition of HCl, $H_3PO_4$, $H_2SO_4$, HBr, etc.

Additionally, salts obtained by reaction from the carboxylic function or acid groups within the phthalocyanine ring are within the scope of the present invention. Such salts include, for example, salts of carboxylic and sulfonic acid with amine derivatives, basic amino acids and inorganic bases.

The present compounds possess both value as PDT agents themselves and also allows for their binding to carrier structures able to recognize biological targets involved in diseases, thus for the preparation of target specific derivatives. The compounds having formula (I) have utility as PDT dyes for treatment of infectious diseases of viral, fungal and bacterial origin, for use in cancer therapy and for dermatological diseases, moreover they may have applications as diagnostic aid in localizing pathologically affected areas.

By conventional chemistry, the mono-carboxy phthalocyanines are convertible to a wide range of aliphatic and aromatic esters or amides, bearing one or more substituents on the alkyl or aromatic groups. Derivatives include esters, amides, amino acids, peptides, proteins (in particular antibodies), sugars, aptamers, sulfonic acid esters, etc. Phthalocyanines polyhydroxylated derivatives, such as glycosides compounds containing mono or polysaccharides, are of great utility as PDT agents, since the resultant derivatives are hydrophilic in contrast to the more hydrophobic phthalocyanines lacking such substituents. As hydrophobic and hydrophilic phthalocyanines concentrate selectively at different sites in a cellular environment, they may have useful applications.

By conventional chemistry the amino phthalocyanines are converted to alkyl, alicyclic, arilalkyl or aromatic secondary and tertiary amines or to amides. The primary amino substituent may also be converted to a diazonium salt and, by subsequent displacement reactions, halo and related derivatives are obtained. The amino group of mono amino substituted phthalocyanine also facilitates easy linkage of the phthalocyanine ring to peptides and proteins with the accompanying transport and binding benefits described above.

Of particular interest are the phthalocyanine derivatives in which amino groups not involved in the linkage with the carrier are further converted to quaternary ammonium salts with various alkylating agents, since for these compound selective activity against Gram −/+ or yeasts micro-organism have been found.

By using solid phase organic synthesis strategies, it is possible to bind the phthalocyanine moiety to a pre-assembled side chain protected polypeptide or polynucleotide attached to a solid phase, allowing for a specific binding of phthalocyanine to the N-terminal of peptide or nucleotide with no disturbance to its structure, thus improving the overall recognition of the target.

As it can be seen from formula (I), the phthalocyanine derivatives object of this invention are aromatic compounds exhibiting improved absorption and singlet oxygen photosensitization characteristics. These compounds contain substituents able to improve their photosensitizing properties and/or to cause a red shift in their light absorption, while retaining the photodynamic characteristics. These compounds have a side chain capable of attachment to predetermined functional groups, which serves as an handle for attachment to protein or to others carriers which may recognize a specific target on a biological structure.

Either the substituents introduced or the conjugation of the phthalocyanines with proteins may accelerate metabolism of the phthalocyanine moiety by interaction with light, thus destroying in vivo the light absorbing chromophore, in order to generate non-photoactivatable metabolites which are photochemically innocuous and thus unable to cause post-PDT phototoxicity.

For example, the presence of hydrophilic substituents and the conjugation is able to accelerate the elimination of those molecules that have not reached the in vivo target. The absorbing chromophore can be eliminated in vivo, thus avoiding the insurgence of delayed cutaneous or systemic toxicity, generating not-photoactivatable, not toxic photodecomposition products.

Derivatives such as quaternary ammonium salts or sulphonate salts are also important, since cationic and anionic dyes are able to concentrate in different areas of cells. Phthalocyanines covalently bound through peptide linkages to peptides or proteins provide PDT agents with valuable specific transport and selective binding characteristics.

Compounds of the present invention are therefore superior to simple derivatized phthalocyanines, with regard to rapid clearance from the body after administration. They are also superior with regards to the toxicity after conjugation to specific carriers, because of the minor dosage due to the specific localization in the ill area.

A major improvement of the molecules object of the present invention is the red shifted absorption they have. Red light of wavelength higher than 670 nm is very much suitable for safe treatment of various diseases. Since light of wavelength lower than 650 nm loses most of its energy after penetrating into human tissues, higher wavelengths are more appropriate than short-penetrating lower wavelengths for dye activation, in applications such as tumours and infectious diseases not superficially located.

The conjugation to macromolecules provides a way to further increase the maximum wavelength absorbance.

Compounds which can be used for conjugation with the phthalocyanines according to the invention are for example: amino acids, peptides, proteins, antibodies, glycosides, aptamers; for example: Avidine, Concanavalin A, Succinil Concanavalin A, Monoclonal and recombinant Antibodies or fragments thereof etc. Further, since the transport, mobility, binding to cell receptors is matter related to chemical structure and, in particular, to the hydrophilic or hydrophobic character of the dye, it is clearly beneficial to have an available primary chemical structure which can be subject to extensive chemical structural manipulation.

When the compound contains a linked amino acid, a peptide or a protein, they are generally bonded to the compounds by means of an amide, thioether, disulfide or an ester linkage. For example, an amino acid may be bound through a carboxyl group on the phthalocyanine, by means of the alpha-amino or other amino group present in the amino acid to form an amide linkage, or the amino group on the phthalocyanine can be bound to the carboxyl group present on the amino acid.

Suitable amino acids include the 20 naturally occurring amino acids in both the R and S forms, as well as non naturally occurring synthetic amino acids.

Peptides may be similarly bound to the ring structure of phthalocyanine and generally contain 2–20 amino acids, although a complete protein (especially the ones showing specificity for a target) may be used as carriers.

The phthalocyanine may be linked to proteins by the above mentioned carboxyl or amino groups or by using other specific functional groups as thiols, maleimide derivatives, alpha bromo esters and amides, diazonium salts and azide derivatives.

In the phthalocyanine glycosides derivatives, the sugar moiety, which may consists of a single sugar, either in the open or cyclic form, an oligosaccharide or a polysaccharide, may be attached to the phthalocyanine ring system by means of a conventional glycoside bond. Any of the common monosaccharide sugars and oligosaccharides thereof may be used to prepare the phthalocyanine glycosides of the present invention.

By using closely related conventional chemistry, conjugates constituted by the phthalocyanine derivatives described and aptamers can be prepared.

All of the many possible derivatives embrace the intact macrocyclic phtalocyanine chromophore and all are capable of generating singlet oxygen or radicals under appropriate irradiation conditions, each constituting therefore a prospective photoactivatable dye for use in PDT.

Using the above described procedure, the following products were obtained; in particular in Examples 1–15 amino reactive compounds (i.e. compounds wherein R is a group capable of reacting with an amino-group) are described, in Example 16, R is a group capable of reacting with Tyr and His, in Examples 17–19 biotine functionalised derivative are described, in Examples 20–21 R, is a group capable of reacting with a thiol-group and in Example 23, R is a group capable of reacting with a carbohydrate. In Example 23, R is a group capable of forming ester linkages with carboxyl groups.

EXAMPLE 1

2-[(4-hydroxycarbonyl)phenoxy]-{[9,10][16,17][23,24]-tribenzo}zinc(II)phthalo cyanine. $C_{51}H_{26}N_8O_3Zn$; green-blue solid; UV-vis (DMF) $\lambda_{max}$ 746, 725, 339;ESI-MS, m/z 863 [M+H]$^+$.

EXAMPLE 2

2-[(4-hydroxycarbonyl)phenoxy]-9(10),16(17),23(24)-tri [2-(morfolin-1-yl) ethoxy]zinc(II) phthalocyanine. $C_{57}H_{53}N_{11}O_9Zn$; green-blue solid; UV-vis (DMF) $\lambda_{max}$ 678, 611, 358, 276; $^1$H-NMR (DMSOd$_6$), δ 9.5–9.3 (m, 1H), 9.3–9.0 (m, 4H), 9.0–8.8 (m, 3H), 8.2–8.0 (m, 2H), 7.8–7.6 (m, 4H), 7.5–7.3 (m, 2H), 4.8–4.5 (m, 6H), 3.85–3.65 (m, 12H), 3.1–2.9 (m, 6H), 2.8–2.6 (m, 12H); ESI-MS m/z 1100.6 [M+H]$^+$, 987.6 [M+C$_6$H$_{13}$NO]$^+$.

EXAMPLE 3

2-[(4-hydroxycarbonyl)phenoxy]-2(3),9(10),16(17),23 (24)-tri[2 -(piperidin-1-yl) ethoxy] zinc(II)phthalocyanine. C$_{60}$H$_{59}$N$_{11}$O$_6$Zn; UV-vis (DMF) $\lambda_{max}$, ($\epsilon$, M$^{-1}$ cm$^{-1}$) 678 (1.308×10$^5$), 612, 355; $^1$H NMR (DMSO-d$_6$) δ 9.55–8.60 (m, 10 H), 8.00–7.55 (m, 6 H), 4.95–4.35 (m, 6 H), 3.10–2.80 (m, 6 H), 2.80–2.35 (m, 12 H), 1.85–1.35 (m, 18 H); ESI-MS m/z 1094.7 [M+H]$^+$.

EXAMPLE 4

2-[(4-hydroxycarbonyl)phenoxy]-1(4),8(11),15(18),22 (25)-tri[2 -(morfolin-1-yl) ethoxy] zinc(II)phthalocyanine. C$_{57}$H$_{53}$N$_{11}$O$_9$Zn; green-blue solid; UV-vis (DMF) $\lambda_{max}$ 762, 691, 623, 340, 268, 259; $^1$H-NMR (DMSOd$_6$) δ 9.5–8.6(m, 4H), 8.3–7.1 (m, 12H), 5.2–5.0(m, 2H), 5.0–4.75(m, 4H), 3.75–3.65(m, 8H), 3.65–3.5(m, 4H), 3.3–3.15(m, 2H), 3.0–22.85(m,8H), 2.8–2.7(m, 4H); FAB-MS m/z 1101 [M+H]$^+$, 987 [M+C$_6$H$_{13}$NO]$^+$.

EXAMPLE 5

2-[(4-hydroxycarbonyl)phenoxy]-9(10),16(17),23(24)-tri [3-(dimethylamino) phenoxy] zinc(II)phthalocyanine. C$_{63}$H$_{47}$N$_{11}$O$_6$Zn; green-blue solid; UV-vis (DMF) $\lambda_{max}$ ($\epsilon$, M$^{-1}$ cm$^{-1}$) 678 (1.4680×10$^5$), 632, 611, 355; $^1$H NMR (DMSO-d$_6$) δ 9.35–8.90(m, 4 H), 8.85–8.50(m, 3 H), 7.95–7.48(m, 7 H), 7.52–7.25(m, 5 H), 6.95–6.55(m, 9 H), 3.10–2.80(m, 18 H); FAB-MS m/z 1118 [M+H]$^+$.

EXAMPLE 6

2-[(4-hydroxycarbonyl)phenoxy]-8(11),15(18),22(25)tri [3-(dimethylamino) phenoxy] zinc(II)phthalocyanine. C$_{63}$H$_{47}$N$_{11}$O$_6$Zn; green-blue solid; UV-vis (DMF) $\lambda_{max}$ ($\epsilon$, M$^{-1}$ cm$^{-1}$) 689 (1.5064×10$^5$), 620, 333; $^1$H NMR (DMSO-d$_6$) δ 9.50–8.70(m, 6 H), 8.68–7.72 (m, 6H), 7.58–6.95(m, 5H), 6.85–6.45(m, 9 H), 6.40–6.30(m, 2 H), 3.10–2.79 (m, 18 H); FAB-MS m/z 1118 [M+H]$^+$.

EXAMPLE 7

2-[(4-hydroxycarbonyl)phenoxy]-9(10),16(17),23(24)-tri [3-(trimethylammonium) phenoxy]zinc(II)phthalocyanine triiodide. C$_{66}$H$_{56}$I$_3$N$_{11}$O$_6$Zn; green-blue solid.

EXAMPLE 8

2-[(4-hydroxycarbonyl)phenoxy]-8(11),15(18),22(25)-tri [3-(trimethylammonium) phenoxy]zinc(II) phthalocyanine triiodide. C$_{66}$H$_{56}$I$_3$N$_{11}$O$_6$Zn; green-blue solid; UV-vis (DMF) $\lambda_{max}$ 689, 620, 333; ESI-MS m/z 388 [M–31$^-$]$^{3+}$.

EXAMPLE 9

2-[(4-hydroxycarbonyl)phenoxy]zinc(II)phthalocyanine. C$_{39}$H$_{21}$N$_8$O$_3$Zn; blue solid; UV-vis (DMF) $\lambda_{max}$ 669, 606, 343; $^1$H NMR (DMSO-d$_6$) δ 9.32–9.14(m, 7 H), 8.77 (broad s, 1 H), 8.26–8.18(m, 8 H), 7.96–7.90 (dd, 1 H, J$_1$=8.67 Hz, J$_2$=1.73 Hz), 7.53(d, 1 H, J=8.59 Hz).

EXAMPLE 10

2-[(4-hydroxycarbonyl)phenoxy]-9,10,16,17,23,24-esa [3-(dimethylamino)phenoxy]zinc(II)phthalocyanine. C$_{87}$H$_{74}$N$_{14}$O$_9$Zn; green-blue solid; FAB-MS m/z 1524 [M$^+$].

EXAMPLE 11

2-[(4-hydroxycarbonyl)phenoxy]-9,10,16,17,23,24-esa [3-(trimethylammonium) phenoxy]zinc(II)phthalocyanine esaiodide. C$_{93}$H$_{92}$I$_6$N$_{14}$O$_9$Zn; green-blue solid.

EXAMPLE 12

2-[(4-sulphonate)phenoxy]-9,10,16,17,23,24-esa[3-(dimethylamino)phenoxy]zinc(II) phthalocyanine. C$_{86}$H$_{74}$N$_{14}$O$_{10}$SZn; green-blue solid; ESI-MS m/z 1562 [(M+H)$^+$].

EXAMPLE 13

2-[(4-sulphonate)phenoxy]-9,10,16,17,23,24-esa[3-(trimethylammonium)phenoxy]zinc(II)phthalocyanine esaiodide. C$_{92}$H$_{92}$I$_6$N$_{14}$O$_{10}$SZn; green-blue solid.

EXAMPLE 14

2-[(4-hydroxycarbonyl)phenoxy]-9,10,16,17,23,24-esa [2-(N,N-diethylamino) ethylthio]zinc(II)phthalocyanine. C$_{75}$H$_{98}$N$_{14}$O$_3$S$_6$Zn; green-blue solid.

EXAMPLE 15

2-[(4-hydroxycarbonyl)phenoxy]-9,10,16,17,23,24-esa [2-(N,N,N-triethylammonium) ethylthio]zinc(II)phthalocyan esaiodide. C$_{81}$H$_{116}$I$_6$N$_{14}$O$_3$S$_6$Zn; green-blue solid.

EXAMPLE 16

2-[(4-aminobenzamidyl)-phenoxy]-8(11),15(18),22(25)-tri[3-(trimethylammonium) phenoxy] zinc(II) phthalocyanine triiodide $\lambda_{max}$ 668, 607, 345, Blue crystals

EXAMPLE 17

N,N'-dimethyl-N-2-(4-oxybenzoyl)-8(11),15(18),22(25)-tri[3-(trimethylammonium) phenoxy] zinc(II) phthalocyanine N'-biotinyl-1,2-diaminoethane triiodide; $\lambda_{max}$ 669, 605, 344, Deep blue crystals.

EXAMPLE 18

N,N'-dimethyl-N-2-(4-oxybenzoyl) zinc(II) phthalocyanine N'-biotinyl-1,2-diaminoethane. Green-blue solid.

EXAMPLE 19

N,N'-dimethyl-N-2-(4-oxybenzoxyl)-9,10,16,17,23,24-esa[3-(trimethylammonium) phenoxy]zinc(II) phthalocyanine N'-biotinyl-1,2-diaminoethane esaiodide. Green-blue solid.

EXAMPLE 20

2-[(4-bromomethylcarbonyl)-phenoxy]-8(11),15(18),22 (25)-tri[3 -(trimethylammonium) phenoxy] zinc(II) phthalocyanine triiodide

EXAMPLE 21

2-[(4-maleimidomethyl)-phenoxy]-8(11),15(18),22(25)-tri[3-(trimethylammonium) phenoxy] zinc(II) phthalocyanine triiodide

EXAMPLE 22

2-[(4-hydrazidomethyl)-phenoxy]-8(11),15(18),22(25)-tri[3-(trimethylammonium) phenoxy] zinc(II) phthalocyanine triiodide; $\lambda_{max}$ 669, 605, 344, Blue crystals.

EXAMPLE 23

2-[(2-hydroxy)ethyoxy]zinc(II) phthalocyanine. $C_{34}H_{20}N_8O_2Zn$, green-blue solid.

CONJUGATES

EXAMPLE 24

Compound of Ex.9-Bovine Serum Albumin (BSA)

12.5 and 25 equivalents of the succinimidyl ester of compound according to Ex. 9 (previously prepared by reacting the corresponding asymmetric anhydride with N-hydroxysuccinimido esters) as DMSO solution, are slowly added to 200 μl of a 5 mg/ml solution of bovine serum albumin (BSA) in PBS (pH=8.5) maintaining the obtained suspension under gentle stirring at room temperature for 90 minutes.

The green-blue conjugation product is purified from the solution by gel filtration (Sephadex G25) eluting with PBS (pH=7.2), collecting fractions having a volume of ca. 1 ml. The labelling ratio has been determined spectrophotometrically measuring the protein concentration and the number of moles of the compound of Ex. 9 per mole of BSA. In the practiced experimental conditions the labelling ratio resulted comprised between 4.2 and 5.0.

Compound of Ex. 7-Avidine

100 μl of a 1.54 mg/ml solution of the succinimidyl ester of compound of Ex. 7 in DMSO are added to 2 mg of avidine (4 mg/ml in 100 mM PBS pH=8.5). The obtained suspension is gently stirred for 12 hours at 4° C., then centrifuged. A purification step is carried out by gel filtration (Sephadex G25) eluting with 100 mM PBS (pH=8.4), collecting the coloured fractions, from which the conjugation product is recovered. The labelling ratio, determined as reported in the preceding Example.16 was 7.

Analogously the following conjugates were prepared:

Compound of Ex. 8-Concanavalin A

100 μl of a solution of the succinimidyl ester of the compound of Ex. 8, 1.5 mg/ml in DMSO are slowly added to 2 mg of concanavalin A (Sigma) solubilized in 0.25 ml of 100 mM phosphate biuffer (pH: 8). The obtained suspension is gently stirred for one night at 4° C. in the dark. After centrifugation the supernatant is purified by gel filtration on Sephadex G25 collecting the fractions showing a characteristic fluorescence. The conjugate has been characterised in terms of moles of phthalocyanine per mole of protein, value turned out to range between 3 and 7

Compound of Ex. 8-Succinil Concanavalin A

The procedure is as reported for Concanavalin A. The ratio was found to range from 3to 5.

Compound of Ex.4- Antibody

Monoclonal Antibody α-D specific for the repeat D of type III FN like of human Tenascin (TN) (Balza et al. FEBS, 332,39 1993) has been labelled by using the compound of Ex. 4.

The labelling procedure has been carried out with the monoclonal bound to the Sepharose 4b immobilised antigen, represented from the recombinant TN containing repeats B,C,D type III FN-like. The labelling ratio Mab/Compound of Ex. 4 was found to be 1:5.

After labelling the binding specificity of the labelled antibody was determined by immunohystochemistry on human fibroblasts (GM6114) and found to be the same of the unlabelled one. Compound of Ex. 4 and the labelling procedure used does not cause aggregation to occur or protein denaturation as demonstrated by the above immuno hystochemistry experiments and can therefore be used to produce photoactives immunoconjugates.

Compound of Ex 7 Peptides Labelling on Solid Phase

Peptides were assembled using FMOC chemistry and various resins suitable for this type of synthesis. The compound of Ex. 7 was coupled to the N terminus of the peptide, branched peptides or loligomers by first activating its carboxylic group with 0.5 molar equiv. of dicycloexylcarbodiimide in DMF overnight at room temperature or alternatively after having formed a mixed anhydride or a succinimidyl esther. The activated compound (5 times molar excess to the N terminal amino groups) was added to the peptide resin in the dark and left to proceed for 24 h at room temperature. The Compound of Ex.7-peptides were cleaved from the resin, worked up by using the solid phase synthesis standard procedures and desalted by using G10 or G25 according to the need and PBS pH: 7.2.The conjugated were analyzed either by mass spectrometry and by their amino acid composition and found consistent with the expected figures.

Compound of Ex. 12 Peptides Labelling in Solution

Compound of Ex. 12 (thiol directed phthalocyanine derivative) was solubilized in DMF and directly added in the dark to a solution of cysteine elongated: peptides, branched peptides and loligomers, in a degassed, nitrogen flushed PBS pH 8.1 solutions. The reaction was left to occur for 24 h at room temperature, then the Compound of Ex.12-peptides were desalted by using G10 or G25 according to the need and PBS pH 7.2.The conjugated were analysed either by mass spectrometry and by their amino acid composition and found consistent with the expected figures.

Biocidal Activity

The lack of non specific toxicity has been assessed by using human fibroblasts cultured for six days. Aliquots of the compound according to Ex. 4 at various concentrations have been added to cells in DMEM 10% FCS. After treatment the cell were irradiated for 10 min with red light (Intralux 4000 equipped with filter BP700/100Chroma Technology Corp.). In a parallel experiment cells were treated with the same amounts of compound of Ex. 4, however no light was provided. No differences in mortality or morphology was detected in comparison to not treated-not irradiated cells up to a 40 μM compound of Ex. 4 concentration.

In a second experiment, not related cell still in DMEM 10% FCS were treated with several aliquots of mAb compound of Ex. 4 conjugated at an equivalent compound of Ex. 4 concentration up to 40 μM. After incubation, the cells were finally exposed for 10 min. to red light (Intralux 4000 equipped with filter BP700/100 Chroma Technology Corp.) and the viability and morphology compared with treated but not irradiated and with not treated, not irradiated cells. No differences were noticed.

Those experiments demonstrate that the compound of Ex. 4 by itself or as mAb conjugated is not toxic for fibroblasts or toward not related cells, well above the standard concentration used to inactivate living form by using PDT.

The usefulness of the compound of the present invention is further demonstrated through their activity against a variety of micro-organisms. The following example refer to the activity against *C. albicans*.

FIG. 1 shows the photoinactivation of *C. albicans* by the compounds according to Ex. 7 and 8 (indicated in the FIGURE with MRLP 090 and MRLP 091 respectively).

Therapetic Formulations

Compounds as previously described may be used either for topical treatment of superficial diseases or after parenteral administration.

Therapeutic compositions containing the compounds of the present invention include liposome or microvesicle preparations, dispersions, ointments, solutions for parenteral injection, etc. and include topical dermatological preparations.

Parenteral Solutions

The photoactivatable phthalocyanines generally are used with additional solvents and adjuvants to prepare solutions suitable for intravenous injection. A number of solvents and co-solvents, that are miscible with water and suitable surfactants, can be used to achieve solutions for parenteral use. The most important solvents in this group are ethanol, polyethylene glycols of the liquid series and propylene glycol. A more comprehensive listing includes dimethyl sulfoxide, ethanol, glycerin, polyethylene glycol 300 and 400, propylene glycol, sorbitol, polyoxyethylene sorbitan fatty acid esters such as laurate, palmitate, stearate, and oleate, polyoxyethylated vegetable oil, sorbitan monopalmitate, 2-pyrrolidone, N-methylpyrrolidine, N-ethylpyrrolidine and tetrahydrofurfuryl alcohol.

Other additives may be necessary to enhance or maintain chemical stability and physiological suitability. Examples are antioxidants, chelating agents, inert gases, buffers and isotonicifiers.

Topical Formulations

The phthalocyanine compounds of the present invention may be formulated for topical application in penetrating solvents or in the form of a lotion, cream, ointment or gel containing a sufficient amount of the phthalocyanine compound to be effective for PDT.

Suitable penetrating solvents are those which will enhance percutaneous penetration of the phthalocyanine compound. Solvents having this property include dimethyl sulfoxide, 1-methyl-2-pyrrolidone, azone and propylene glycol. DMSO solutions containing 0–50 wt. % water are particularly desirable.

Liposome or Microvesicle Preparations

Liposomes are microvesicles which encapsulate a liquid within lipid or polymeric membranes; the methods of preparing liposomes for both topical and parenteral (injectable) preparations are known in the art. The phthalocyanine compounds of the present invention having lipophilic characteristic may be incorporated into liposome microvesicles and used in this form for both topical and parenteral application.

Photodynamic therapy using the phthalocyanine compounds of the present invention has a number of advantages. The phthalocyanine compounds itself are minimally toxic in the unexcited state. Each phthalocyanine molecule can be repeatedly photoactivated and leads each time to cell-lethal events, that is the generation of singlet molecular oxygen or radicals. The half-life of singlet oxygen is such that the target cell is affected without the opportunity for migration of the lethal singlet oxygen to neighbouring healthy tissue cells. Singlet oxygen molecules rupture chemical bonds in the cell DNA, target cell wall, or destroy intracellular structures such as mitochondria, resulting in destruction of the target cell. Destruction of target cell tissue commences promptly upon irradiation of the phthalocyanine compounds and ceases abruptly when irradiation is stopped.

Photodynamic therapy using the compounds of the present invention is therefore selective and minimally toxic to healthy tissue. Singlet oxygen molecules produced which do not react rapidly with neighboring molecules rapidly decay.

A variety of phototherapy and irradiation methodologies are known to those skilled in the art and can be used with the novel phthalocyanine compounds of the present invention. The time and duration of therapy and repetition of the irradiation treatment can be selected by the physician according to known photodynamic therapy criteria. The dosage of the phthalocyanine compound may be varied according to the size and location of the target tissues which are to be destroyed and the method of administration. Generally, the dosage will be in the range of 0.1–20 mg of phthalocyanine compound per kilogram of body weight, more preferably in the range of 0.1–5.0 mg/kg.

For cancer therapy ad treatment of infectious diseases, irradiation generally takes place not less than one hour and nor more than four days after administration of the phthalocyanine compound. Usually, phototherapy is begun approximately 10 hours to 24 hours after administration of the photodynamic therapy agent. For dermatological applications like psoriasis, but also for infectious diseases or cancer treatment, radiation therapy can commence immediately after topical application of the phthalocyanine or up to 12 hours later. Systemic application for treatment of dermatological diseases is followed by radiation usually 15 to 24 hours after systemic administration of the PDT agent. Exposure to non therapeutic light sources should be avoided immediately following phototherapy to minimise light toxicity. Appropriate cover of the patient can be used, to limit the area affected by phototherapy.

Light sources appropriate for the use in PDT are well known in the art and may vary from white light sources associated with appropriate filters to lasers settled to the right wavelength. As noted above, preferred wavelengths are from 600 to 950 nm, preferably from about 650 to about 750 nm. The total amount of light which is applied to the affected area will vary with the treatment method used and with the location of the lesion. Generally, the amount of light is in the range of about 50 to 1000 $Jcm^{-2}$, preferably in the range of 100 to 350 $Jcm^{-2}$.

What is claimed is:

1. A metal substituted non-centrosymmetrical phthalocyanine of formula (I):

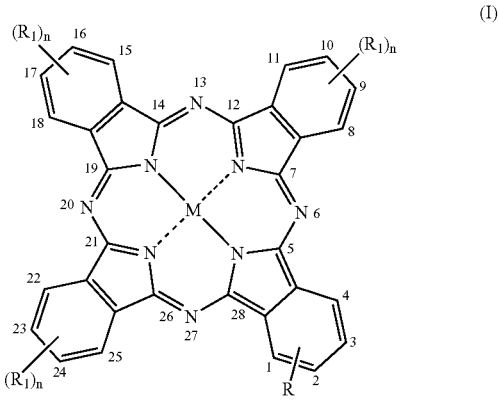

wherein:
n is 1, 2 or 4;
M is selected from the group consisting of Zn, $Si(OR_7)_2$ and $AlOR_7$ wherein $R_7$ is selected from the group consisting of H and $C_{1-15}$ alkyl;
R is selected from the groups consisting of: —COOH, —SH, —OH, —$NH_2$, —CO—$CH_2$—Br, —$SO_2Cl$, maleimide, hydrazide, phenol, imidate, biotine, possibly bound to the phthalocyanine nucleus through a suitable linker and
when n=2 and the two groups $R_1$ are in the positions 9,10,16,17,23,24, said two groups $R_1$ can form a saturated or unsaturated heterocycle, possibly substituted, which may contain up to two heteroatoms chosen from N, O, S; or
$R_1$ is represented by the group $(X)_p R_2$, wherein:
X is selected from the group consisting of O, S, —$NR_5$ and —$CH_2$— and $R_2$ is

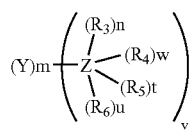

where:
Y is selected from the group consisting of $C_{1-10}$ alkyl and phenyl, possibly substituted, or it forms with the Z group, to which it is bound, a saturated or unsaturated heterocycle, possibly substituted, which may contain up to two heteroatoms selected from the group consisting of N, O and S;
Z is selected from the group consisting of —N, —$CH_2N$ and —$CONHCH_2CH_2N$;
$R_3$ and $R_4$, equal or different from one another, are selected from the group consisting of $C_{1-15}$ alkyl and phenyl, or form with the Z group, to which they are bound, a saturated or unsaturated heterocycle, possibly substituted, which may contain up to two heteroatoms selected from the group consisting of N, O and S;
$R_5$ and $R_6$, equal or different from one another, are selected from the group consisting of H and $C_{1-15}$ alkyl;
m, n, p, w, t and u, independently from one another, are 0 or 1; and
v is an integer comprised between 1 and 3;
with the proviso that:
R is in the position 1 or 2,
$R_1$ is in the positions: 8(11), 15(18), 22(25), or 9(10), 16(17), 23(24) when n=1,
$R_1$ is in the positions: 8,11,15,18,22,25 or 9,10,16,17,23, 24 when n=2.

2. Metal phthalocyanine according to claim 1 wherein M is Zn.

3. Metal phthalocyanine according to claim 1 wherein the group $(X)_p R_2$ is selected from the group consisting of:

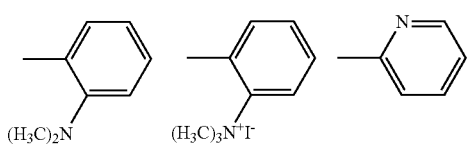

-continued

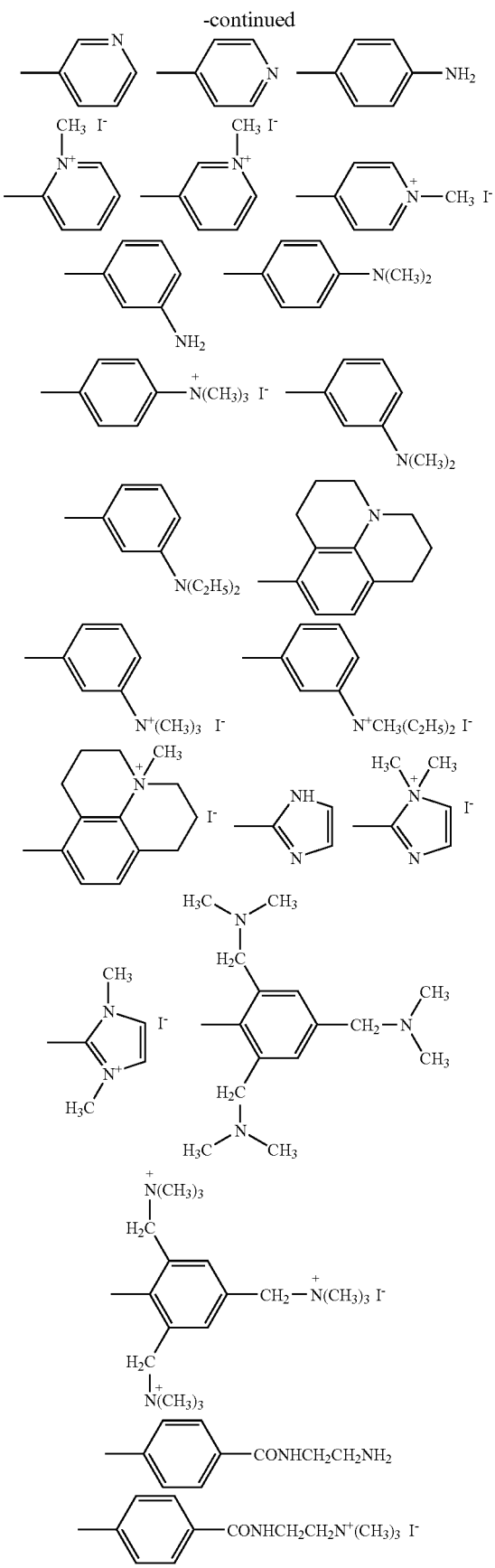

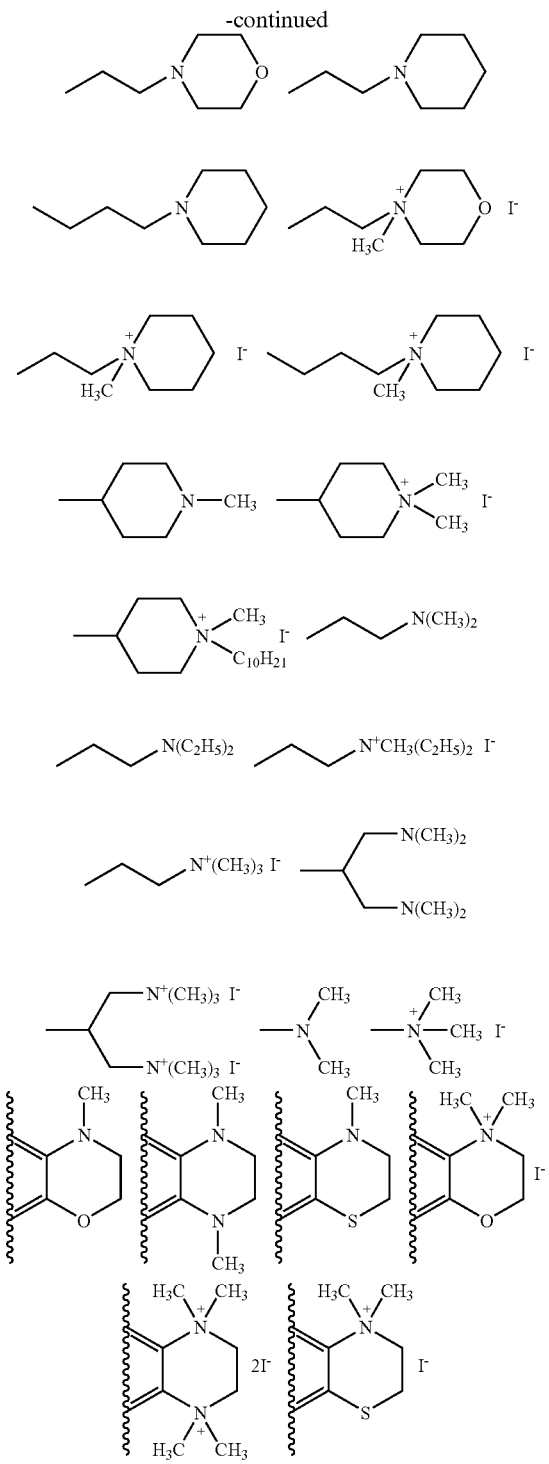

4. The metal phthalocyanine according to claim 1 represented by:

2-[(4-hydroxycarbonyl)phenoxy]-{[9,10][16,17][23,24]-tribenzo}zinc(II)phthalo cyanine;

2-[(4-hydroxycarbonyl)phenoxy]-9(10),16(17),23(24)-tri [2-(morfolin-1-yl) ethoxy]zinc(II)phthalocyanine;

2-[(4-hydroxycarbonyl)phenoxy]-2(3),9(10),16(17),23 (24)-tri[2 -(piperidin-1-yl) ethoxy]zinc(II)phthalocyanine;

2-[(4-hydroxycarbonyl)phenoxy]-1(4),8(11),15(18),22 (25)-tri[2 -(morfolin-1-yl) ethoxy]zinc(II)phthalocyanine;

2-[(4-hydroxycarbonyl)phenoxy]-9(10),16(17),23(24)-tri [3-(dimethylamino) phenoxy]zinc(II)phthalocyanine;

2-[(4-hydroxycarbonyl)phenoxy]-8(11),15(18),22(25)-tri [3-(dimethylamino) phenoxy] zinc(II)phthalocyanine;

2-[(4-hydroxycarbonyl)phenoxy]-9(10),16(17),23(24)-tri [3-(trimethylammonium) -phenoxy]zinc(II)phthalocyanine triiodide;

2-[(4-hydroxycarbonyl)phenoxy]-8(11),15(18),22(25)-tri [3-(trimethylammonium) -phenoxy]zinc(II)phthalocyanine triiodide;

2-[(4-aminobenzamidyl)-phenoxy]-8(11),15(18),22(25)-tri[3-(trimethylammonium) phenoxy]zinc(II)phthalocyanine triiodide;

N,N'-dimethyl-N-2-(4-oxybenzoxy)-8(11),15(18),22(25)-tri[3-(trimethylammonium) phenoxy]zinc(II)phthalocyanine N'-biotinyl-1,2-diaminoethane triiodide;

2-[(4-bromomethylcarbonyl)-phenoxy]-8(11),15(18),22 (25)-tri[3-(trimethylammonium) phenoxy]zinc(II)phthalocyanine triiodide;

2-[(4-maleimidomethyl)-phenoxy]-8(11),15(18),22(25)-tri[3-(trimethylammonium) -phenoxy]zinc(II)phthalocyanine triiodide;

2-[(4-hydrazidomethyl)-phenoxy]-8(11),15(18),22(25)-tri[3-(trimethylammonium) -phenoxy]zinc(II)phthalocyanine triiodide;

2-[(4-hydroxycarbonyl)phenoxy]-9,10,16,17,23,24-esa [3-(dimethylamino) phenoxy]zinc(II)phthalocyanine;

2-[(4-hydroxycarbonyl)phenoxy]-9,10,16,17,23,24-esa [3-(trimethylammonium) -phenoxy]zinc(II)phthalocyanine esaiodide;

2-[(4-sulphonate)phenoxy]-9,10,16,17,23,24-esa[3-(dimethylamino) phenoxy]zinc(II)phthalocyanine;

2-[(4-sulphonate)phenoxy]-9,10,16,17,23,24-esa[3-(trimethylammonium) phenoxy]zinc(II)phthalocyanine esaiodide;

2-[(4-hydroxycarbonyl)phenoxy]-9,10,16,17,23,24-esa [2-(N,N-diethylamino) ethylthio]zinc(II)phthalocyanine;

2-[(4-hydroxycarbonyl)phenoxy]-9,10,16,17,23,24-esa [2-(N,N,N-triethylammonium) ethylthio]zinc(II)phthalocyanine esaiodide; and N,N'-dimethyl-N-2-(4-oxybenzoxyl)-9,10,16,17,23,24-esa[3-(trimethylammonium) phenoxy]zinc(II)phthalocyanine N'-biotinyl-1,2-diaminoethane esaiodide.

5. A pharmaceutical composition for use in photodynamic therapy, comprising the meta phthalocyanine according to claim 1, optionally in combination with one or more pharmaceutically acceptable diluents and excipients.

6. The pharmaceutical composition according to claim 5 for the treatment of infectious diseases of viral, fungal and bacterial origin, of diseases characterised by cellular hyperproliferation and of dermatological diseases.

7. The pharmaceutical composition according to claim 5 in the form of a liposome or microvesicle preparation, dispersion, ointment, solution for parenteral injection, or topical dermatological preparation.

8. A sterilizing agent for blood and blood derivatives comprising a metal substituted non-centrosymmetrical phthalocyanine of formula (I):

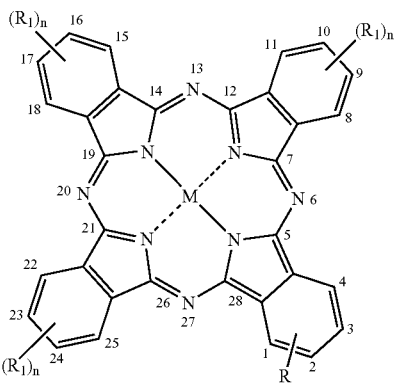

wherein:

n is 1,2 or 4;

M is selected from the group consisting of Zn, $Si(OR_7)_2$ and $AlOR_7$ wherein $R_7$ is selected from the group consisting of H and $C_{1-15}$ alkyl;

R is selected from the groups consisting of: —COOH, —SH, —OH, —$NH_2$, —CO—$CH_2$—Br, —$SO_2Cl$, maleimide, hydrazide, phenol, imidate, biotine, possibly bound to the phthalocyanine nucleus through a suitable linker and when n=2 and the two groups $R_1$ are in the positions 9,10,16,17,23,24, said two groups $R_1$ can form a saturated or unsaturated heterocycle, possibly substituted, which may contain up to two heteroatoms chosen from N, O, S; or $R_1$ is represented by the group $(X)_pR_2$, wherein:

X is selected from the group consisting of O, S, —$NR_5$ and —$CH_2$— and $R_2$ is

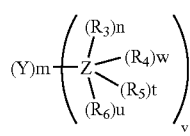

where:

Y is selected from the group consisting of $C_{1-10}$ alkyl and phenyl, possibly substituted, or it forms with the Z group, to which it is bound, a saturated or unsaturated heterocycle, possibly substituted, which may contain up to two heteroatoms selected from the group consisting of N, O and S;

Z is selected from the group consisting of —N, —$CH_2N$ and —$CONHCH_2CH_2N$;

$R_3$ and $R_4$, equal or different from one another, are selected from the group consisting of $C_{1-15}$ alkyl and phenyl, or form with the Z group, to which they are bound, a saturated or unsaturated heterocycle, possibly substituted, which may contain up to two heteroatoms selected from the group consisting of N, O and S;

$R_5$ and $R_6$, equal or different from one another, are selected from the group consisting of H and $C_{1-15}$ alkyl;

m, n, p, w, t and u, independently from one another, are 0 or 1; and v is an integer comprised between 1 and 3;

with the proviso that:

R is in the position 1 or 2,

R1 is in the positions: 8(11), 15(18), 22(25), or 9(10), 16(17), 23(24) when n=1, R1 is in the positions: 8,11,15,18,22,25 or 9,10,16,17,23, 24 when n=2.

9. A diagnostic agent comprising a metal substituted non-centrosymmetrical phthalocyanine of formula (I):

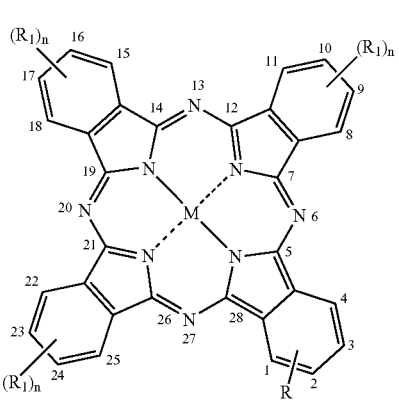

wherein:

n is 1, 2 or 4;

M is selected from the group consisting of Zn, $Si(OR_7)_2$ and $AlOR_7$ wherein $R_7$ is selected from the group consisting of H and $C_{1-15}$ alkyl;

R is selected from the groups consisting of: —COOH, —SH, —OH, —$NH_2$, —CO—$CH_2$—Br, —$SO_2Cl$, maleimide, hydrazide, phenol, imidate, biotine, possibly bound to the phthalocyanine nucleus through a suitable linker and when n=2 and the two groups $R_1$ are in the positions 9,10,16,17,23,24, said two groups $R_1$ can form a saturated or unsaturated heterocycle, possibly substituted, which may contain up to two heteroatoms chosen from N, O, S; or $R_1$ is represented by the group $(X)_pR_2$, wherein:

X is selected from the group consisting of O, S, —$NR_5$ and —$CH_2$— and $R_2$ is

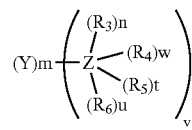

where:

Y is selected from the group consisting of $C_{1-10}$ alkyl and phenyl, possibly substituted, or it forms with the Z group, to which it is bound, a saturated or unsaturated heterocycle, possibly substituted, which may contain up to two heteroatoms selected from the group consisting of N, O and S;

Z is selected from the group consisting of —N, —CH$_2$N and —CONHCH$_2$CH$_2$N;

R$_3$ and R$_4$, equal or different from one another, are selected from the group consisting of C$_{1-15}$ alkyl and phenyl, or form with the Z group, to which they are bound, a saturated or unsaturated heterocycle, possibly substituted, which may contain up to two heteroatoms selected from the group consisting of N, O and S;

R$_5$ and R$_6$, equal or different from one another, are selected from the group consisting of H and C$_{1-15}$ alkyl;

m, n, p, w, t and u, independently from one another, are 0 or 1;and v is an integer comprised between 1 and 3;

with the proviso that:

R is in the position 1 or 2,

R1 is in the positions: 8(11), 15(18), 22(25), or 9(10), 16(17), 23(24) when n=1, R1 is in the positions: 8,11,15,18,22,25 or 9,10,16,17,23, 24 when n=2.

10. A method of treating infectious diseases of fungal origin caused by *Candida albicans*, comprising administering to a patient in need of such treatment an effective amount of a metal phthalocyanine according to claim 1.

11. A method of localizing areas pathologically affected by infectious diseases of fungal origin caused by *Candida albicans*, comprising administering to a patient an effective amount of a metal phthalocyanine according to claim 1.

* * * * *